United States Patent
Heath et al.

(10) Patent No.: US 11,530,580 B2
(45) Date of Patent: Dec. 20, 2022

(54) PROBE ARRAYS FOR MONITORING WELLBORE FLUID COMPOSITION AND METHODS OF USING THE SAME

(71) Applicant: Newpark Drilling Fluids LLC, The Woodlands, TX (US)

(72) Inventors: Garett Heath, Calgary (CA); Dylan James Hadley, Calgary (CA)

(73) Assignee: Newpark Drilling Fluids LLC, The Woodlands, TX (US)

( * ) Notice: Subject to any disclaimer, the term of this patent is extended or adjusted under 35 U.S.C. 154(b) by 38 days.

(21) Appl. No.: 17/148,306

(22) Filed: Jan. 13, 2021

(65) Prior Publication Data

US 2021/0215036 A1 Jul. 15, 2021

Related U.S. Application Data

(60) Provisional application No. 62/961,001, filed on Jan. 14, 2020.

(51) Int. Cl.
*E21B 21/01* (2006.01)
(52) U.S. Cl.
CPC .................................. *E21B 21/01* (2013.01)
(58) Field of Classification Search
CPC ........... E21B 21/01; E21B 21/08; E21B 47/01
See application file for complete search history.

(56) References Cited

U.S. PATENT DOCUMENTS

| | | | | |
|---|---|---|---|---|
| 6,257,354 | B1* | 7/2001 | Schrader | G01F 23/296 175/48 |
| 6,357,536 | B1* | 3/2002 | Schrader | G01N 11/08 175/48 |
| 7,823,656 | B1* | 11/2010 | Williams | E21B 21/01 175/38 |
| 2011/0061866 | A1* | 3/2011 | Patel | E21B 21/00 166/270.1 |
| 2014/0048331 | A1* | 2/2014 | Boutalbi | E21B 21/001 175/38 |
| 2017/0073565 | A1* | 3/2017 | McDaniel | E21B 7/00 |
| 2017/0260820 | A1* | 9/2017 | Sehsah | F04B 15/02 |
| 2019/0330938 | A1* | 10/2019 | Askelsen | C02F 11/14 |
| 2019/0376355 | A1* | 12/2019 | Sickels | E21B 21/08 |
| 2020/0166478 | A1* | 5/2020 | Mohr | G01N 33/2847 |
| 2020/0270958 | A1* | 8/2020 | Omrani | E21B 37/00 |
| 2021/0131234 | A1* | 5/2021 | Lopes Pereira | E21B 21/06 |

* cited by examiner

*Primary Examiner* — Brad Harcourt
(74) *Attorney, Agent, or Firm* — John Wilson Jones; Jones Delflache LLP

(57) ABSTRACT

Methods include the use of a probe array that includes a flotation device configured to maintain the probe array adjacent a surface of a wellbore fluid; an acquisition module secured to the flotation device such that the acquisition module is positioned below the surface of the wellbore fluid, and that include one or more of a dissolved oxygen probe, a pH probe, a turbidity probe, or a conductivity probe; transmitter configured to receive data acquired from the acquisition module and transmit the data to a computer system configured to receive the data from the transmitter and configured to perform the steps of: processing the data to determine one or more wellbore fluid properties, displaying the one or more wellbore fluid properties and/or one or more remedial actions.

20 Claims, 13 Drawing Sheets

PROBE ARRAYS FOR MONITORING WELLBORE FLUID COMPOSITION AND METHODS OF USING THE SAME

BACKGROUND OF THE DISCLOSURE

Wellbore operations in subterranean formations involve the management of large volumes of wellbore fluids. During drilling, wellbore fluids are circulated downhole and perform various tasks including lubrication of the drill bit, transporting drill cuttings, and maintaining hydrostatic pressure against the formation. As wellbore fluid is continually pumped downhole, displaced fluids return to the surface along with entrained solids, gases, and connate fluids encountered downhole.

The accumulated materials change the properties of the wellbore fluid, which can result in changes in the performance, including reduced rate of penetration, loss of mud downhole and filter cake buildup. In addition, wellbore fluids can encounter corrosive materials during drilling and production operations, which can degrade downhole equipment, particularly metal components. Adverse changes in wellbore fluid composition can affect the quality of the of the well, the drilling speed, cost to drill to depth, sticking of a drill bit, cave in potential, and the overall yield of the well. Corrosive gases, such as $H_2S$ and $CO_2$, and abrasive particulates can degrade metal equipment, which can lead to reduced equipment performance and eventual failure. Degraded performance and unexpected equipment failure can lead to undesirable downtime of drilling operations and costs associated with repaired affected equipment.

To mitigate changes in wellbore fluid composition and corrosivity, wellbore fluids are collected upon return to the surface and reconditioned in stages to remove contaminants, including solids, fines, and gases. Wellbore fluids can also be treated with additives to remove emulsions and flocculate solids, and to replenish brines and other materials depleted downhole or removed with unwanted contaminants. Treated fluids are then transferred to suction tanks to be circulated back downhole.

Wellbore fluid reconditioning requires analysis of fluid properties to identify the presence of contaminants, and to verify that reconditioning methods are effective in maintaining fluid characteristics within desired performance limits. However, traditional wellbore fluid measurement techniques involve manual sampling at inconsistent time intervals in laboratories that are on site or remote, or through the use of specialized and expensive equipment integrated into downhole equipment. For example, wellbore fluid measurements can involve the use of tethered logging tools lowered into a wellbore suspended on a cable or pushed into the wellbore using, for example, coiled tubing, or pushed or pulled along the wellbore using a tractor, or other similar driving mechanism. Conventional tethered logging tools and the cable or wiring attached thereto are generally bulky, requiring specialized vehicles or equipment and a specialized crew of technicians to deploy and operate. The need to mobilize specialized vehicles and/or other large equipment and to provide a crew of technicians to remote well sites increases the expense associated with well logging and can introduce undesirable delays in obtaining needed data.

Thus, there is a need for improved monitoring and fluid property measurement devices capable of monitoring locations within a surface wellbore fluid circulating system in real-time to track changes in fluid composition during wellbore operations.

DETAILED DESCRIPTION

Figure 1:
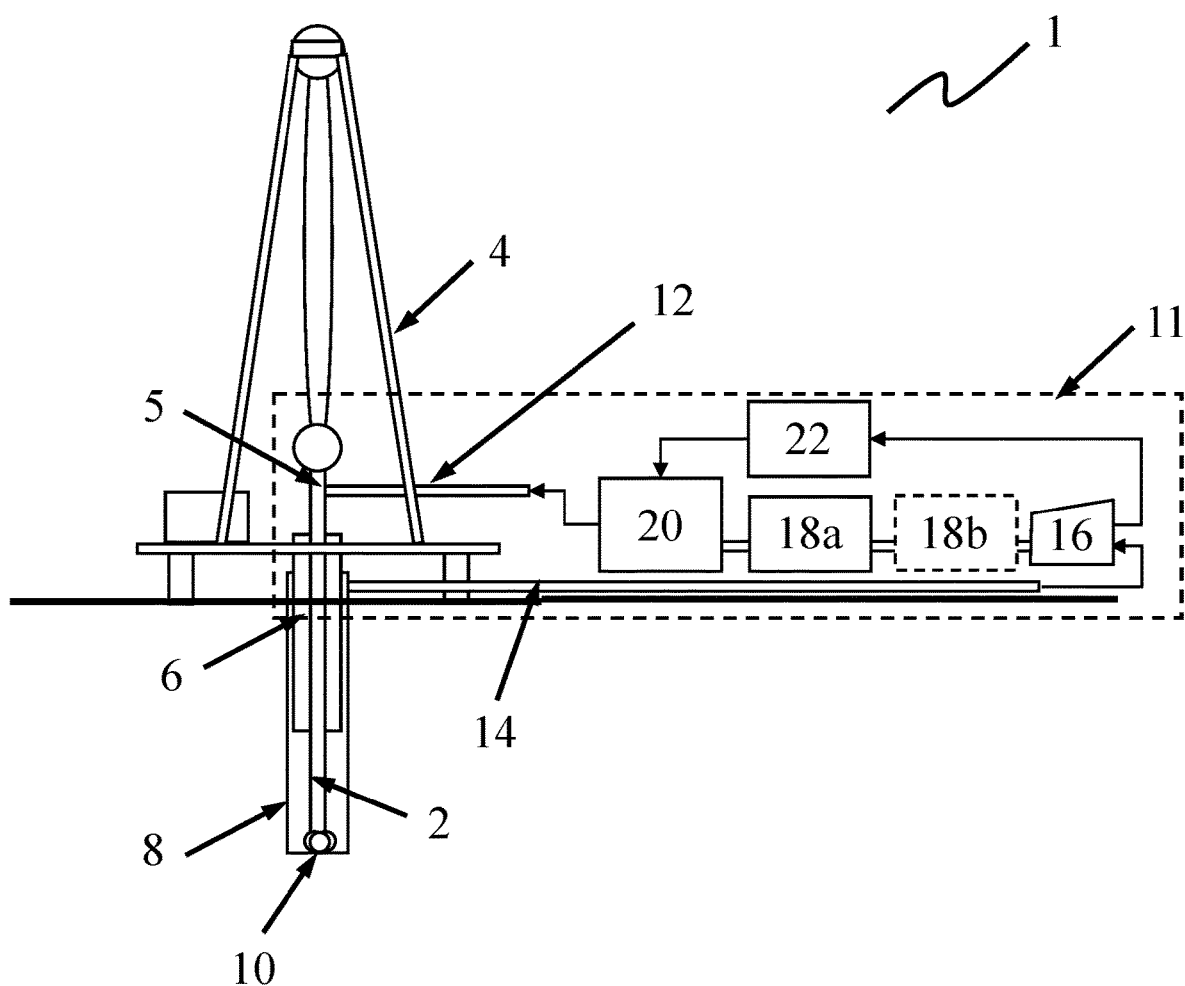
FIG. 1 is a schematic depicting a surface wellbore fluid circulating system in accordance with the present disclosure.

Provided herein is a probe array that can be positioned at various locations and in various tanks at a drill site. In an aspect, the probe array can be positioned in a surface wellbore fluid circulating system to monitor wellbore fluid composition and obtain instantaneous and/or real-time feedback. In an aspect, the probe array can be positioned in the surface wellbore fluid circulating system in any wellbore construction operation, including injection wells and production wells, including natural resource production wells such as hydrogen sulfide, hydrocarbons or geothermal wells. The probe array of the present disclosure can be emplaced within the surface wellbore fluid circulating system and provide data regarding fluid properties of wellbore fluids without the need for downhole measurements or the use of expensive specialized equipment designed to withstand downhole operating conditions. The probe array of the present disclosure can be portable and modular.

In an aspect, the probe array can include an acquisition module having one or more probes, including probes to measure turbidity (solids content), pH, oxygen and conductivity (density). The probe array can be constructed to include a flotation device that maintains the device at the surface of wellbore fluid in a pit or tank being monitored, even as fluid levels increase or decrease. The probe array of the present disclosure can be used to identify changes in wellbore fluid/mud composition over time, which can be an indicator of adverse conditions. For example, changes in oxygen concentration, pH, salt concentration, and solids can indicate corrosive conditions that can increase equipment wear and premature failure. Elevated levels of dissolved oxygen can also be associated with foam formation that can affect density, rheology, and fluid performance Spikes in dissolved oxygen levels can also indicate that air is entering the system as fluid volumes in one or more tanks or pits are depleting due to fluid losses downhole or at the surface. Conductivity measurements can be used to identify changes in fluid density and signal the need to recondition the wellbore fluid with additional brine or salts.

The probe array can enable direct measurement within wellbore fluid tanks, which minimizes errors associated with sampling and transporting fluids. The probe array can be configured as portable devices that is installed within the surface wellbore fluid circulating system, providing a flexible platform for analyzing fluid conditions in one or more locations during wellbore operations. The probe array can be placed at various locations in the system to optimize process steps, such as optimizing solids removal or minimizing air intrusion. In an aspect, the probe array can be emplaced in a suction tank or other vessel near the point in which a wellbore fluid enters a wellbore. The agitation within the suction tank also reduces coagulation of fines that can affect the measurement of some fluid properties. The probe array can also be emplaced at other locations such as flocculation tanks to monitor flocculant efficiency.

The probe array can be used to provide instantaneous and/or real-time measurements in the surface wellbore fluid circulating system. In an aspect, real-time measurement of the surface wellbore fluid circulating system can be used in conjunction with performance limits, such as a limit of dissolved oxygen, turbidity, pH, or conductivity, to notify an operator when or before alarm conditions are reached. The probe array can be used in conjunction with monitoring software that can include custom programs or commercially available packages. In an aspect, fluid properties collected over time can also be constructed as algorithms used to predictively to determine when wellbore fluid reconditioning is needed or when fluid-handling equipment failure to corrosion is likely.

General Drilling Setup

The probe array 26 can be used to monitor fluid properties in the surface wellbore fluid circulating system 11 on site and in one or more locations of the system. With particular respect to FIG. 1, a well site 1 is shown having a drilling tower 4 constructed on over a subterranean well 8. During the drilling operation, drilling mud is pumped by means of a mud pump (not shown) from the suction tank 20 through a mud supply line 12 to a swivel connector 5. The swivel connector 5 and a drill string 2 are hollow and mud is pumped down to a drill bit 10 at the bottom of the well 8. The mud then proceeds back up through the annular space between the drill string 2 and the sides of the well 8 into the surface wellbore fluid circulating system 11, which can include a series of fluid handling tanks and/or pits that process the mud and redirect the mud back into the drill string 2 and the well 8. In an aspect, mud can also be redirected to storage or disposal once drilling operations are completed.

As the mud returns to the surface from the well 8, it is directed by a mud return line 14 to a first fluid separation system 16 that may include one or more shale shakers. The first fluid separation system 16 can separate solids and fines from the mud. The first fluid separation system 16 can comprise other solids control equipment in addition to or instead of shale shakers, including but not limited to centrifuges, cuttings dryers, electrophoresis, vacuum, or combinations thereof. After solids removal, mud is transferred to a settling tank 18a. At some well sites 1, a second settling tank 18b can be incorporated, depending on the need for further solids separation and reconditioning. In other configurations, mud can be transferred from the first fluid separation system 16 to a flocculation tank 22, where the mud is reconditioned with flocculants and other additives to remove entrained solids and contaminants After flocculation, mud can be discharged back into the settling tank 18a (to allow more settling time) or directly into the suction tank 20 to shorten system volumes and minimize treatable volumes.

In an aspect, gaseous contaminants introduced into drilling muds can be removed using degassers, such as vacuum degassers, and similar equipment. Following solids and gas removal, mud then passes from the settling tank 18a or the flocculation tank 22 to the suction tank 20 and recirculated back to the mud supply line 12. In an aspect, mud can also be collected and transferred to a storage tank or pit (not shown) for reclamation or disposal. Depending on the wellbore application, the well site 1 can include additional flocculation tanks or mixing tanks for treatment.

FIG. 1 is provided as an example only, and it is envisioned that devices and methods of the present disclosure can be adapted to other configurations and for different wellbore operations, including fracturing, completions, and mining. In an aspect, devices of the present disclosure can be employed in wellbore operations having a variable number and type of tanks that can depend, for example, on the depth and type of wellbore. Wellbore operations can include the use of one or more settling or flocculation tanks, storage tanks, mixing tanks, and suction tanks arranged in any number of configurations.

During wellbore operations, mud in the surface wellbore fluid circulating system 11 can change in composition over time as the fluid is admixed with fluids and solids encountered downhole, or as components are removed with cuttings and treatments during reconditioning and recirculation. Changes in composition and fluid properties can be monitored by placing the probe array 26 in a tank or pit in the flow path of the surface wellbore fluid circulating system 11.

Figure 2:
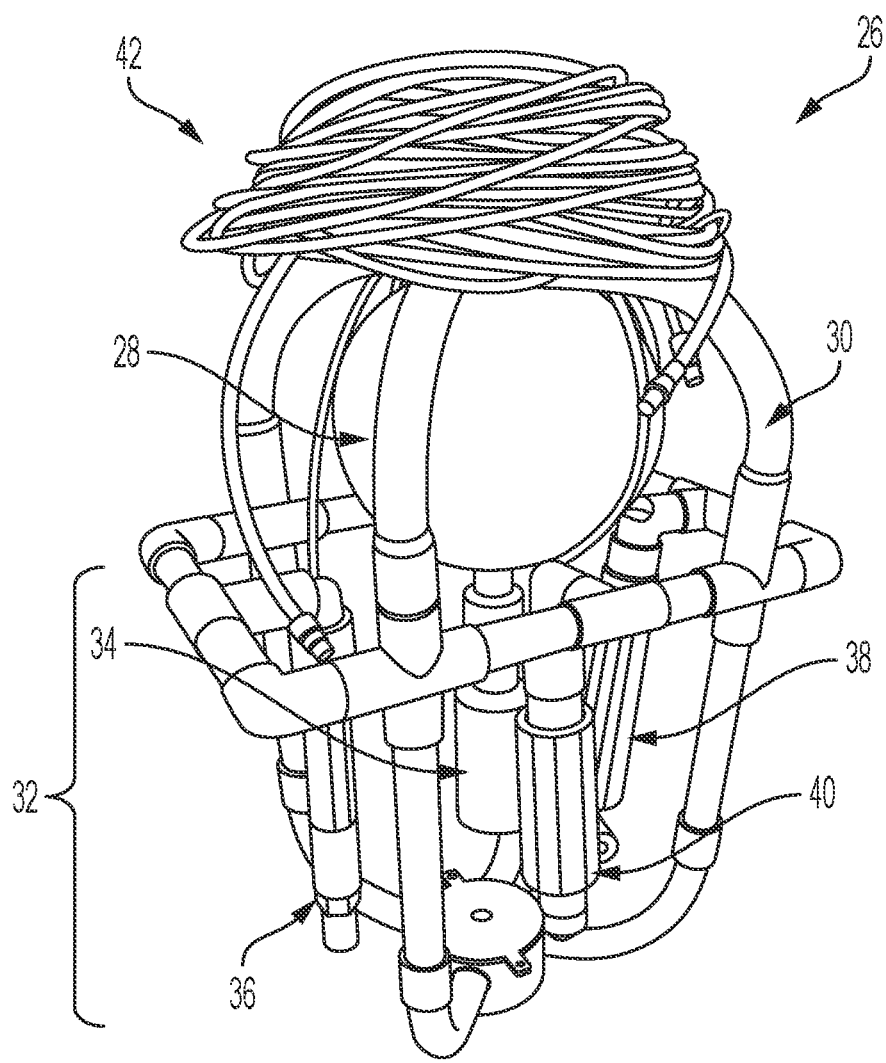
FIG. 2 illustrates a probe array device in accordance with the present disclosure.

With particular respect to FIG. 2, the probe array 26 is shown. The probe array 26 can include the flotation device 28 surrounded by a protective cage 30. The probe array 26 also includes the flotation device 28 that maintains the probe array 26 position adjacent the surface level of a wellbore fluid even with changes in fluid level in a tank or pit. The flotation device 28 can include any structure containing a buoyant material (solid, liquid, gas, or mixtures) having a density lower than the surrounding wellbore fluid, including inflatables, bladders, pontoons, tanks, foams, cellular materials, buoys, and the like.

The protective cage 30 provides impact protection for the flotation device 28 and the acquisition module 32. The protective cage 30 can include hollow and/or solid structural supports that allow fluid into the interior of the probe array 26 to contact the acquisition module 32, including a frame and/or mesh screen, for example. Components of the protective cage 30 can be prepared from any material including plastic, composites, or metal.

The acquisition module 32 is positioned below the flotation device 28 and configured to remain submerged when the probe array 26 is emplaced within a wellbore fluid. The acquisition module 32 can include one or more separate measurement probes, such as a dissolved oxygen probe 34, a pH probe 36, a turbidity probe 38, and a conductivity probe 40. The probe array 26 can be modular, where each probe can be independently separated and/or replaced for various purposes including maintenance. Data collected from the acquisition module 32 can be transferred by data cables 42 to a device for data recording and/or transmission to a computer system for processing and display of results.

Figure 3A:
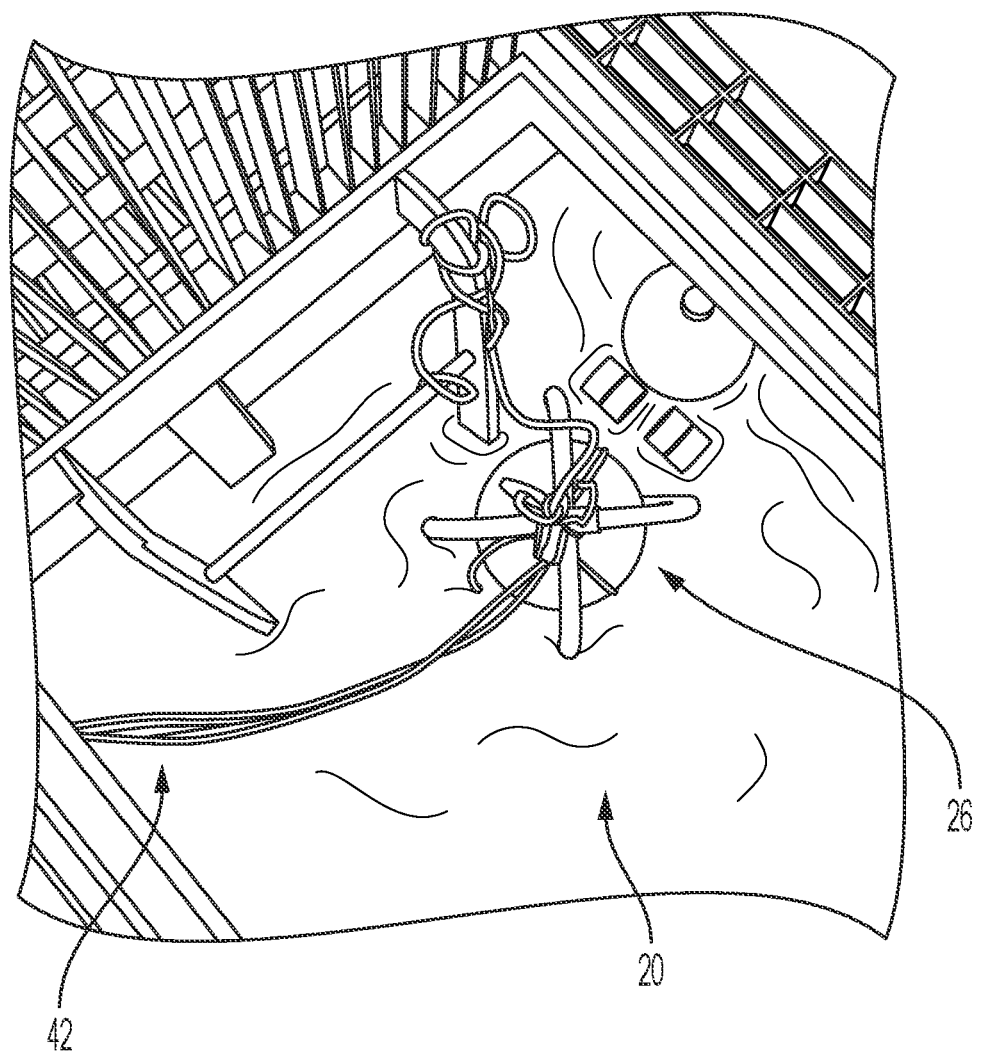
FIGS. 3A and 3B illustrate a probe array device in accordance with the present disclosure deployed in a suction tank.
Figure 3B:
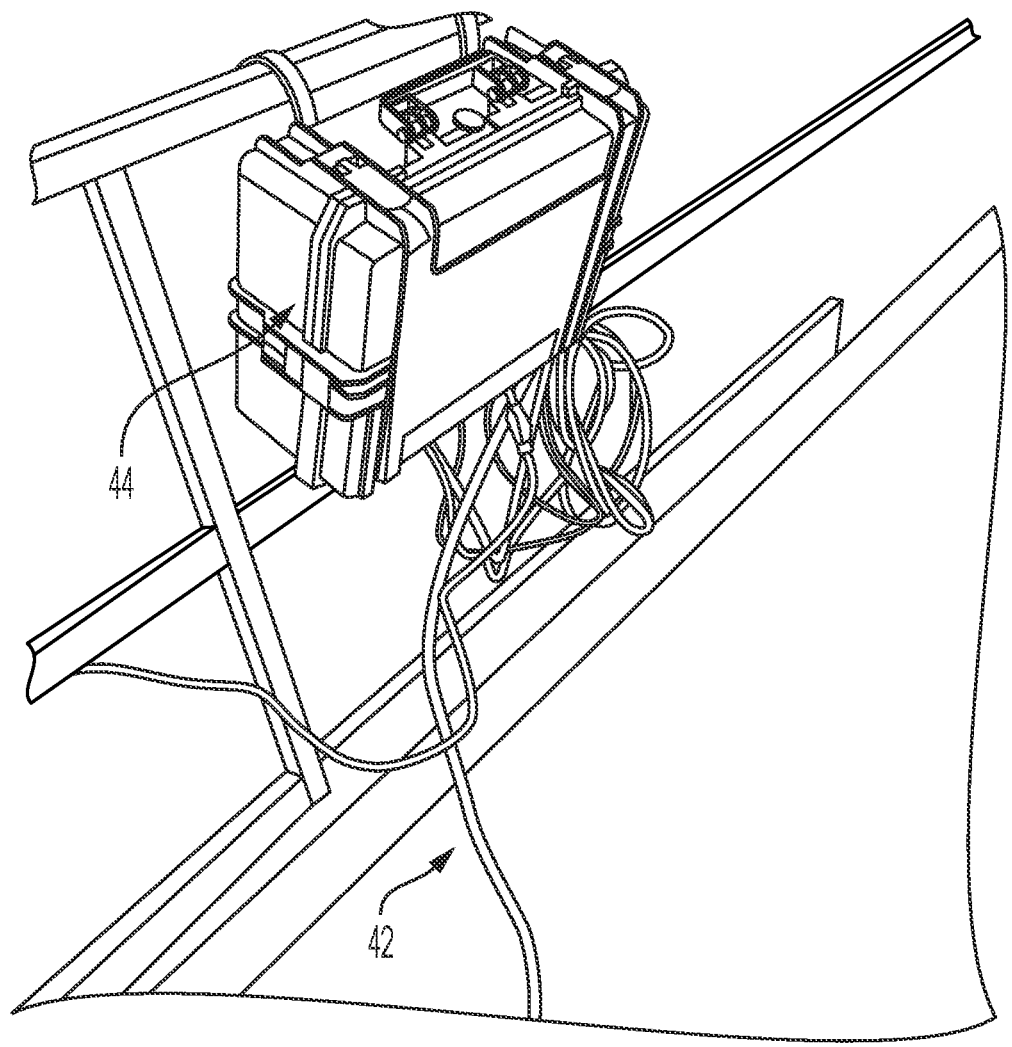

In an aspect, the probe array 26 can be deployed in a tank within the surface wellbore fluid circulating system 11, such as the suction tank 20, the settling tank 18a, or the flocculation tank 22 to provide instantaneous and real-time feedback for fluid properties of wellbore fluids within the surface wellbore fluid circulating system 11 and being pumped into the well 8. With particular respect to FIG. 3A, the probe array 26 is shown deployed in the suction tank 20 of the surface wellbore fluid circulating system 11. In this example, the probe array 26 records and transmits recorded data through the data cables 42 to a transmitter 44, shown in FIG. 3B, or other device for data recording and/or transmission. In an aspect, the acquisition module 32 can be configured to transmit data wirelessly to the transmitter 44 or other device without the data cables 42.

The probe array 26 can measure and record data using an onboard computer system coupled to the acquisition module 32 or by sending data obtained from the acquisition module 32 to an external computer system, such as a computer system coupled to the transmitter 44. For the purposes of this disclosure, "coupled" as used herein is intended to mean coupling of components or subsystems in a way to permit communication of information between the components or subsystems. Two components or subsystems may be communicatively coupled through a wired or wireless communication network, including but not limited to Ethernet, LAN, fiber optics, radio, microwaves, Bluetooth, satellite, and the like. Operation and use of such communication networks is well known to those of ordinary skill in the art and will, therefore, not be discussed in detail herein.

Data transmitted from the acquisition module 32 can be communicated as single or continuous measurements. In an aspect, measurements can be obtained in continuous or real-time for a selected time period, or measurements can be obtained intermittently or for regular intervals. Measurement probes incorporated in the acquisition module 32 can acquire measurements in intervals that range between fractions of a second to days. In an aspect, measurement intervals can range from 0.1 second to 1 day. Measurement intervals can also be faster or slower depending on the probe type and application requirements.

Acquisition Modules

The probe array 26 can include the acquisition module 32 that includes one or more probes to measure fluid properties of a wellbore fluid disposed in a tank or pit of the surface wellbore fluid circulating system 11. Measurement probes are modular and can be installed and swapped at the well site 1, depending on the particular application, providing a flexible platform for fluid analysis and monitoring. Probes and various probe types are available from commercial suppliers, including probes suitable for monitoring water, brine, and/or emulsion quality, such as Hach® probes. Commercial probes include nitrate probes, ammonia probes, organic amine probes, ion selective probes (including cation and anion probes such as calcium, magnesium, barium, strontium, nitrate probes, sulfate, carbonate and orthophosphates), silica probes and redox probes (ORP).

The acquisition module 32 can be equipped to monitor various fluid properties of wellbore fluids, including chemical compositions of the water or brine mixtures, and aqueous mixtures containing various amounts of organic liquids such as hydrocarbons and lubricants, and dissolved oxygen content. Fluid properties also include physical properties such as conductivity, pH, density, viscosity, water hardness, internal phase ratio, the optical properties of water or brine such as turbidity, absorption, refractive index, fluorescence, the presence of corrosive conditions, corrosion rate, scale-forming conditions, concentration of chemical additives such as corrosion inhibitors, scale inhibitors, oxygen scavengers, lost circulation materials, emulsifiers, and other wellbore fluid conditioning treatments.

Other acquisition modules can include probes to measure emulsion strength, capacitance, dielectric constant, impedance, loss tangent, reactance phase angle, acoustic attenuation, acoustic relaxation, thermal conductivity, electrical conductivity, salinity, oil content, solids content, water content, and any combination thereof. The probes used to measure these properties also may include any known sensing or measurement equipment, including but not limited to thermistors, transducers, cameras, UV, spectrography, light emitting diodes (LED), luminescence, electrodes, differential internal fluids and sensors (such as pH), ultrasound, ionic exchange and ion-selective membranes, auto-titration, sludge level sensors, flow sensors, optical sensors, retort devices, and any combinations thereof. In an aspect, a guided wave radar system or other level sensor device may be used to detect separated layers of oil or aqueous fluids, and properties regarding the size and/or nature of those layers may be measured.

In the following sections a number of possible probes are discussed, however, it is envisioned that other probe types measuring similar fluid properties can be incorporated into the acquisition module 32 of the present disclosure.

Dissolved Oxygen Probe

The acquisition module 32 can be equipped with the dissolved oxygen probe 34 that calculates the dissolved oxygen in solution, such as the amount of oxygen in a unit volume of water (mg/L or ppm). Use of the probe array 26 enables users to measure dissolved oxygen levels directly, minimizing errors associated with obtaining and transferring fluid samples during manual on site measurement.

The presence of oxygen can increase corrosion conditions and indicate the formation of foams and corresponding changes in rheological properties. The dissolved oxygen probe 34 can identify system points where oxygen is being introduced, and can be used as an indicator for various remedial actions, such as the addition of oxygen scavengers or increasing fluid levels to minimize splashing or air intrusion into exposed drains. In an aspect, the dissolved oxygen probe 34 can include a commercially available probe, such as the 9020000-SW dissolved oxygen probe from Hach®.

Turbidity Probe

The acquisition module 32 can be equipped with the turbidity probe 38 that can quantify or measure the concentration of suspended fine colloidal particles that do not settle out of solution and increase cloudiness. The turbidity probe 38 can include a measurement by nephelometer, which measures the relative amount of light able to pass through a solution, and is reported as NTU (Nephelometric Turbidity Units). Turbidity can also be expressed in terms of percent solids.

Increased turbidity can indicate an increase in the level of circulating fines, which can increase the abrasion against fluid handling equipment and enhance chemical damage due to scale and corrosion. The turbidity probe 38 can indicate that flocculants and other chemical additives are needed to flocculate and remove solids, or can indicate that solids removal equipment is in need of servicing. Turbidity and percent solids can also be used in conjunction with the pH probe 36 to adjust the pH within the surface wellbore fluid circulating system 11 to optimize a selected flocculant or indicate a need to switch types of flocculant. For example, an increase in turbidity even when the pH is steady can indicate a need to switch from an anionic flocculant to a cationic flocculant or neutral flocculant. In an aspect, the turbidity probe 38 of the present disclosure can include commercially available probes, such as the LXV423.99.10100 turbidity probe from Hach®.

pH Probe

The acquisition module 32 can be equipped with the pH probe 36 that analyzes the acidity or basicity of a wellbore fluid. The measurement of pH is a method of expressing hydrogen ion concentration logarithmically with the pH value being the negative logarithm (base 10) of the hydrogen ion concentration. Determination of pH provides an indicator of solubility of various components in a wellbore fluid such as salts and a number of chemical additives. For wellbore fluids, a pH lower than ~7 can be associated with corrosive and redox conditions that can damage metal surfaces and decrease the solubility of flocculants and other additives. The addition of caustics or acids are used to increase or decrease pH, respectively. In an aspect, the pH probe 36 of the present disclosure can include commercially available probes, such as the DPD1P1 pH probe from Hach®.

Conductivity Probe

The acquisition module 32 can be equipped with the conductivity probe 40 that quantifies the ability of a wellbore fluid to transmit electricity. Conductivity increases with increasing ion concentration, but does not identify a specific ion. The basic unit of conductivity is the siemens (S), and because cell geometry affects conductivity values, standardized measurements are often expressed in specific conductivity units (S/cm) to compensate for variations in electrode dimensions. Conductivity measurements can also be used to determine TDS (Total Dissolved Solids).

During wellbore operations, conductivity measurements can indicate the concentration of ions in solution and the ionic strength of the wellbore fluid, which can affect the efficiency of various chemical additives such as flocculants. Conductivity measurements can also be used in conjunction with turbidity to determine density, which can be adjusted by increasing the addition of salts or brine, or reducing density by dilution. Similarly, conductivity measurements can be combined with specific ion measurements, such as calcium, to determine specific salt concentrations, to monitor brine concentrations, for example. In an aspect, the conductivity probe 40 of the present disclosure can include commercially available probes, such as the LXV428.99.00001 conductivity probe from Hach®.

Transmitter

The probe array 26 can transfer data captured from the acquisition module 32 to the transmitter 44 that transmits the data to a computer system present at the well site 1 or at a remote location by any suitable wired or wireless protocol. For example, measurements can be taken in real-time, sent to a cloud or remote computer system, and then processed to determine one or more fluid properties. In an aspect, the transmitter 44 can have an onboard computer system that processes data captured from the acquisition module 32 and/or stores the data on a non-transitory computer-readable medium. In an aspect, the transmitter 44 of the present disclosure can include commercially available transmitters, such as the MSM sc1500 controller from Hach®.

Computer System

Data collected from the probe array 26 can be transferred by the transmitter 44 to a computer system present at the well site 1 or at a remote location that collects, processes, and displays data directly or through a secondary computer system such as a laptop or portable device. Computer systems of the present disclosure include personal computers (e.g., desktop or laptop), tablet computers, mobile devices (e.g., personal digital assistant (PDA) or Smartphone), servers (e.g., blade server or rack server), a network storage devices, or any other suitable computing device and may vary in size, shape, performance, functionality, and price.

Data processing can be performed locally (on site) or by a remote or cloud-based computer system. Data captured from the acquisition module 32 can be recorded and analyzed by computer system in real time, including analysis of the wellbore fluid properties at any point in time and calculation of changes over time. Computer systems can be programmed with instructions to perform various data manipulations including aggregating data from multiple probes and providing composite data, such as density, corrosion rates, or scaling rates.

Computer systems of the present disclosure can store data on any suitable computer-readable media that can include nonvolatile, hard-coded type media, such as read only memories (ROMs), or erasable, electrically programmable read only memories such as EEPROMs or flash memory; recordable type media, such as flash drives, memory sticks, and other newer types of memories; and transmission type media such as digital and analog communication links. For example, such media can include operating instructions, as well as instructions related to the apparatus and the method steps of the present disclosure and can operate on a computer system.

Applications

Methods of the present disclosure include the use of the probe array 26 to determine one or more fluid properties in the surface wellbore fluid circulating system 11. In an aspect, the probe array 26 is used to monitor wellbore fluid quality and the presence of adverse conditions such as corrosion or scale formation. Monitoring of wellbore fluid properties can include comparing data obtained from the probe array 26 with previous measurements obtained from a well being drilled or a database of previously acquired well data to determine whether remedial action is needed and, if so, recommending one or more remedial actions. In an aspect, the probe array 26 data can be presented as graphical data and can be accompanied with notifications and instructions on remedial measures that can be employed.

The probe array 26 can incorporate a number of probes for analyzing wellbore fluid properties, such as dissolved oxygen, pH, turbidity or solids percentage, and conductivity. In an aspect, data from multiple probes can be combined to provide composite data such as density, corrosion rates, or scaling rates. Methods of the present disclosure include the use of the probe array 26 to monitor wellbore fluids in real time and to provide predictive warnings of adverse conditions and equipment failure.

In an aspect, methods of the present disclosure can identify corrosion conditions, including the calculation of corrosion rates, such as milli-inches per year (MPY), that are comparable with immersion corrosion testing done by any field accepted techniques such as ASTM G31. Corrosion conditions are often correlated with reductions in pH, increased turbidity, increased conductivity, and the presence of corrosive chemicals in the wellbore fluid. Methods of the present disclosure also include the use of the probe array 26 to determine the rate of scale formation and/or scale formation conditions by monitoring the concentration of scale forming ions in the wellbore fluid along with correlated factors such as pH and increased turbidity.

Methods of the present disclosure include the use of the probe array 26 that includes the flotation device 28 configured to maintain the probe array 26 adjacent a surface of a wellbore fluid; the acquisition module 32 secured to the flotation device 28 such that the acquisition module 32 is positioned below the surface of the wellbore fluid, and that include one or more of the dissolved oxygen probe 34, the pH probe 36, the turbidity probe 38, or the conductivity probe 40; the transmitter 44 configured to receive data acquired from the acquisition module 32 and transmit the data to a computer system configured to receive the data from the transmitter 44 and configured to perform the steps of: processing the data to determine one or more wellbore fluid properties, displaying the one or more wellbore fluid properties and/or one or more remedial actions. In an aspect, processing the data to determine one or more fluid properties includes determining a corrosion rate.

Methods of the present disclosure include measuring one or more fluid properties of a wellbore fluid in a container (such as a tank, flocculation tank, suction tank, pit, or other vessel) containing the wellbore fluid using the probe array 26, wherein the one or more fluid properties include at least one of dissolved oxygen, pH, turbidity, or conductivity; maintaining the probe array 26 adjacent to a surface of the wellbore fluid; determining a change in the one or more fluid properties of the wellbore fluid over a time interval; and taking a remedial action to change the one or more fluid properties. Determining a change in the one or more fluid properties of the wellbore fluid over a time interval can include determining a corrosion rate. In an aspect, the step of measuring occurs at or adjacent to a location in which the wellbore fluid enters a wellbore.

Remedial Actions

Once adverse conditions have been identified by methods of the present disclosure, one or more remedial actions can be taken. In an aspect, data collected from the probe array 26 can be analyzed by a computer system and used to provide a user with recommendations of possible remedial actions. In an aspect, multiple remedial actions can be provided by a computer system based on user provided constraints of the well site 1, such as material or tool availability, costs, timing, and the like.

Remedial actions used with the present methods and systems may include the use any chemical additives known in the art for treating wellbore fluids. Examples of chemical additives that may be suitable include, but are not limited to, flocculants, surfactants (e.g., foamers, defoamers, emulsifiers, demulsifiers), pH adjusters (e.g., buffers, acids, bases), viscosifiers, biocides, coagulants, corrosion inhibitors, oxygen scavengers, sulfide scavengers, scale inhibitors, and any combinations thereof. In an aspect, remedial actions can involve the addition of chemical additives under varying conditions, such as temperature, shear rate, flow rate, additive concentration, additive dosing rate, residence time (e.g., time that the additive is allowed to react with components of the wellbore fluid before other treatments are performed), and any combinations thereof.

Remedial actions can include identifying corrosion or scale formation conditions and instructing a user to apply an anti-corrosion or anti-scaling treatment or whether to replace a pipe, tubing, or other mechanical component prior to failure.

Remedial actions can include a number of treatments to control or mitigate adverse conditions that can include adjusting one or more of pH, additive concentration, brine concentration, and fluid levels within the surface wellbore fluid circulating system 11. Remedial actions can include the addition of an oxygen scavenger and/or the adjustment of fluid levels to reduce dissolved oxygen levels; adding salts to increase the conductivity of the wellbore fluid or lowering the conductivity through dilution or by adding flocculants and/or chelants to remove ions; adding a flocculant and/or adjusting pH to reduce turbidity; switching types of flocculant to reduce turbidity, such as switching from a cationic flocculant to an anionic flocculant based on pH compatibility; reducing turbidity by adjusting salt concentration and conductivity to enhance flocculant performance; raising pH by caustic addition, such as lime, soda ash, caustic soda, and the like; or lowered using citric acid, muriatic acid, and the like; changing the location of the probe array 26 to improve probe function, such a relocating to a position closer to the well entrance having less solids concentration; and the like.

In an aspect, data obtained from the probe array 26 can be compiled over time and used to develop algorithms to predict wellbore fluid conditions downhole and/or anticipate changes needed to the fluid to increase or maintain operation efficiency and minimize equipment failure rates. Data for individual wells can be formation dependent, and can include information regarding geological composition of the well, well depth, rate of penetration, fluid types, and the like.

EXAMPLES

In the following examples, the probe array 26 is deployed at the well site 1 in the surface wellbore fluid circulating system 11 that includes the suction tank 20 and the flocculation tank 22.

Example 1

In this example, the probe array 26 equipped with the dissolved oxygen probe 34, the pH probe 36, the turbidity probe 38, and the conductivity probe 40 is used to monitor wellbore at a drilling site at various locations in the surface wellbore fluid circulating system 11. Measurements were obtained continuously for two days.

Figure 4:
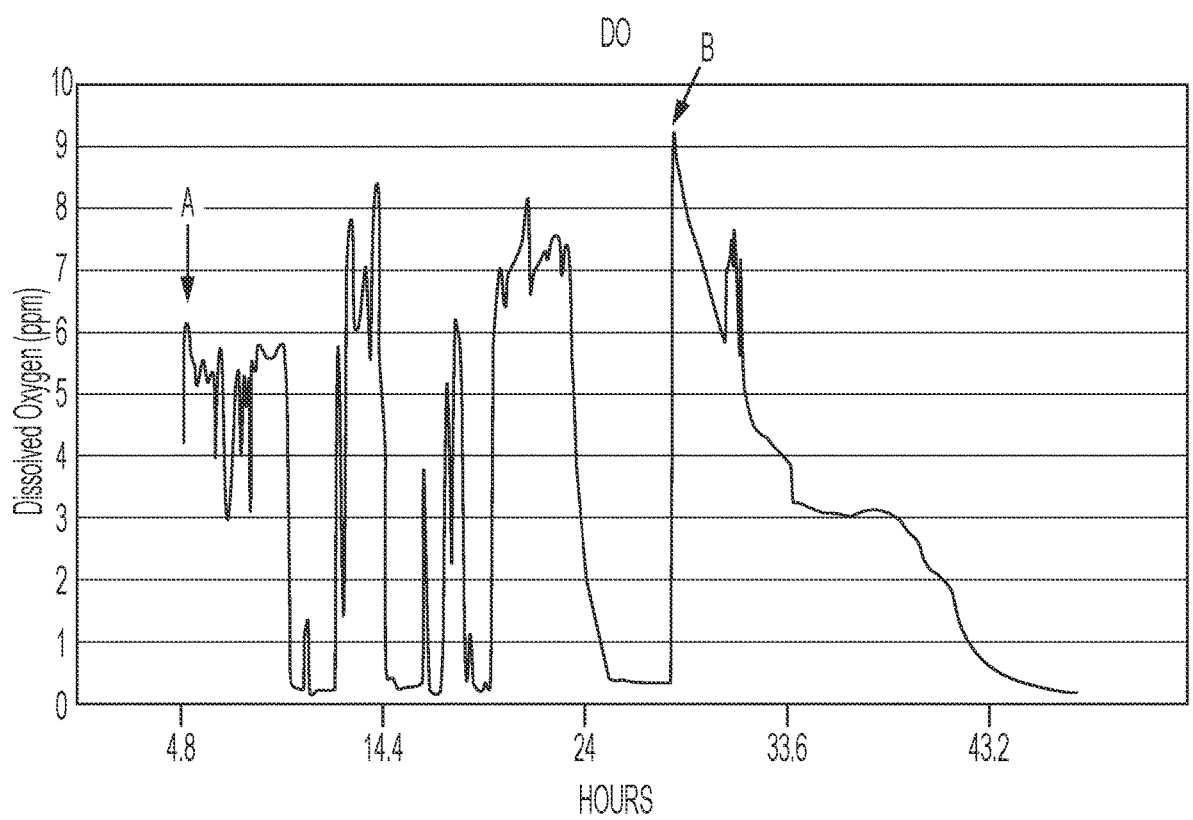
FIG. 4 is a graphical depiction of dissolved oxygen concentration as a function of time obtained from a dissolved oxygen probe in accordance with the present disclosure.

FIG. 4 is a graphical depiction of dissolved oxygen concentration as a function of time obtained from the dissolved oxygen probe 34 in accordance with the present disclosure. FIG. 4 indicates changes in dissolved oxygen content over time, and as the probe array 26 is moved from the suction tank 20 (A) to the flocculation tank 22 (B) in the surface wellbore fluid circulating system 11. Increases in dissolved oxygen indicate the introduction of air into the surface wellbore fluid circulating system 11 through splashing or intrusion into conduits as fluid levels rise and fall in the various tanks along the circulating system flow path.

Figure 5:
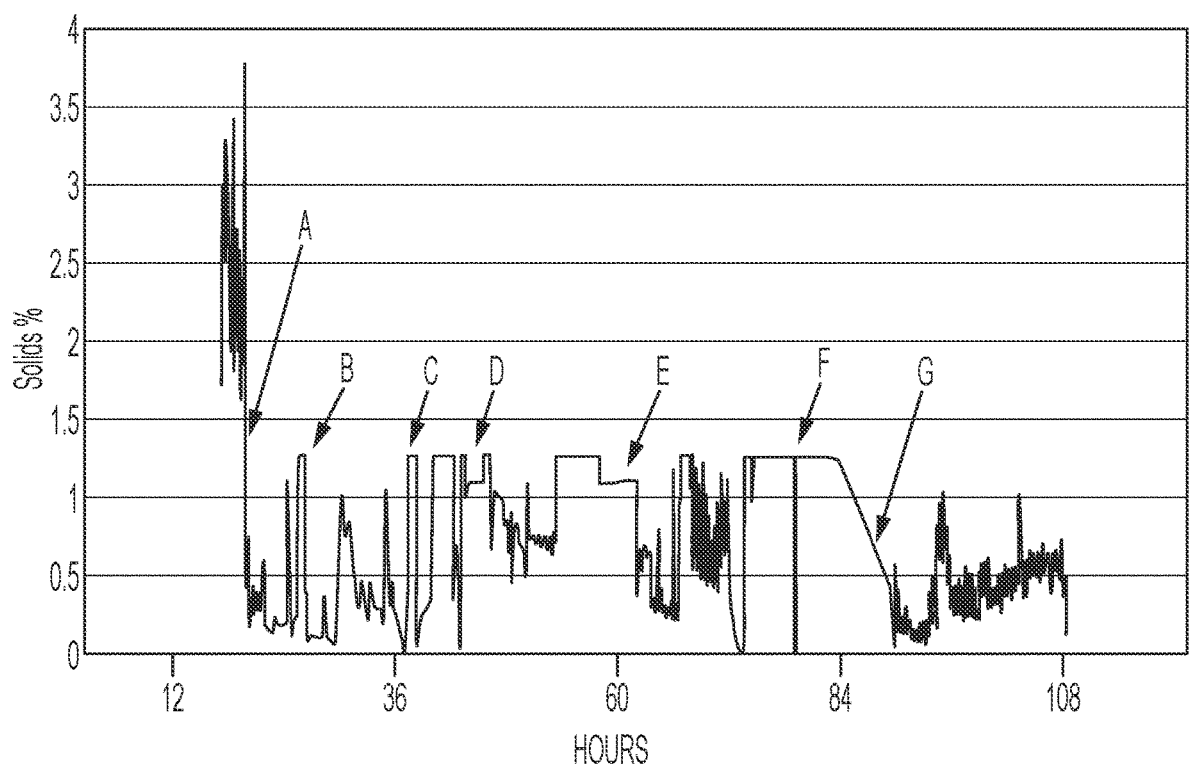
FIG. 5 a graphical depiction of total suspended solids as a function of time obtained from a turbidity probe in accordance with the present disclosure.

With particular respect to FIG. 5, a graphical depiction of total suspended solids as a function of time obtained from the turbidity probe 38 in accordance with the present disclosure. In FIG. 5, the turbidity is measured at seven points A-G along the surface wellbore fluid circulating system 11. The data show that the total suspended solids percentage decreases as the probe array 26 is moved further down the flow path from the first fluid separation system 16 to the suction tank 20. For example, solids percentage decreases from the flocculation tank 22 (D) to the suction tank 20 (G).

Figure 6:
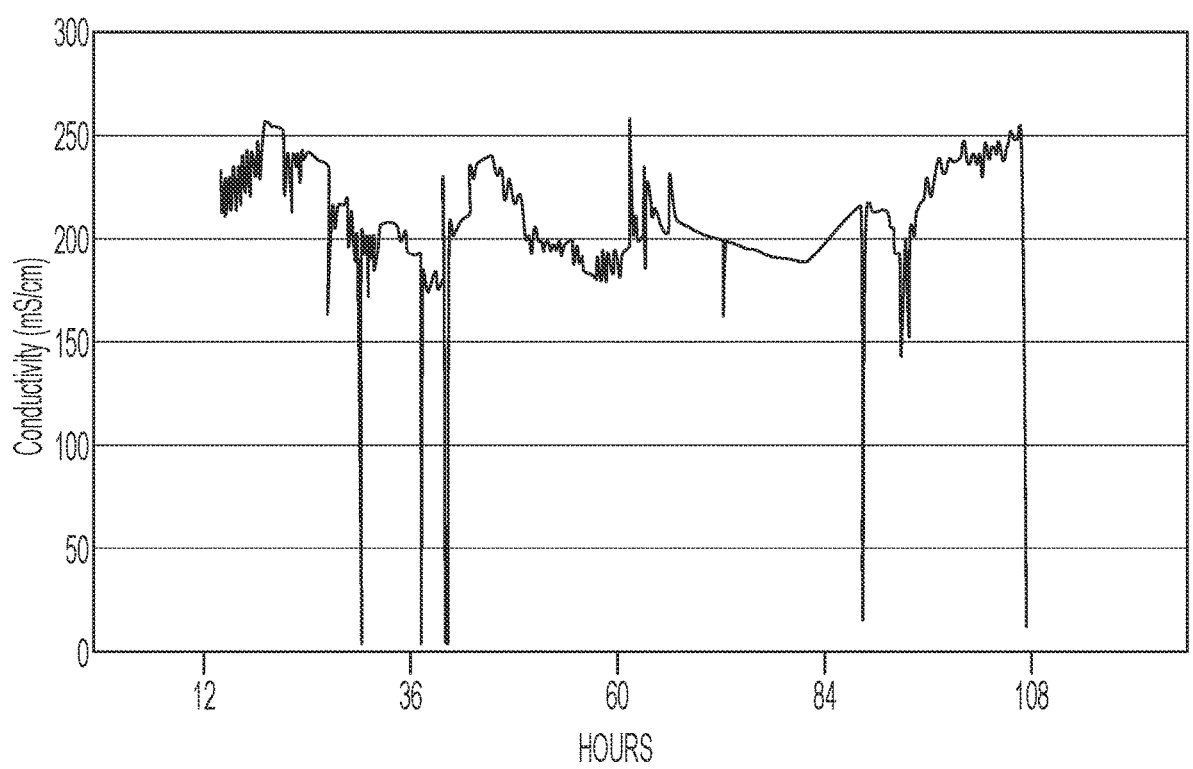
FIG. 6 is a graphical depiction of total conductivity as a function of time obtained from a conductivity probe in accordance with the present disclosure.
Figure 7:
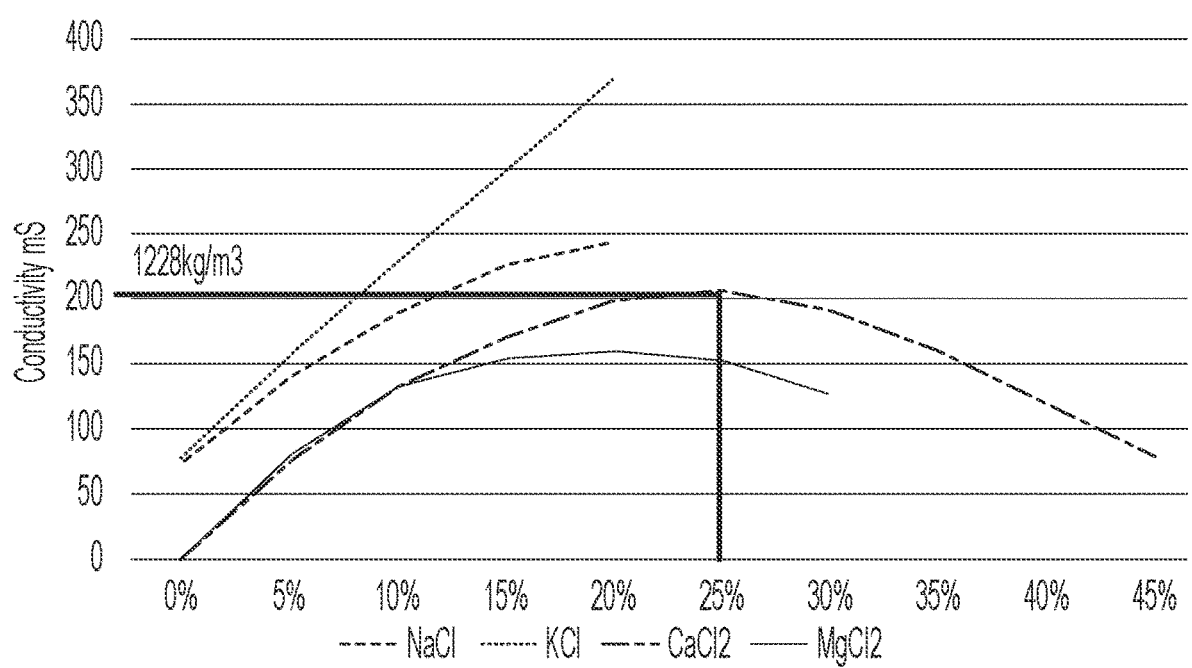
FIG. 7 is a graphical depiction of total conductivity response of a number of exemplary salts as a function of time obtained using a conductivity probe in accordance with the present disclosure.
Figure 8:
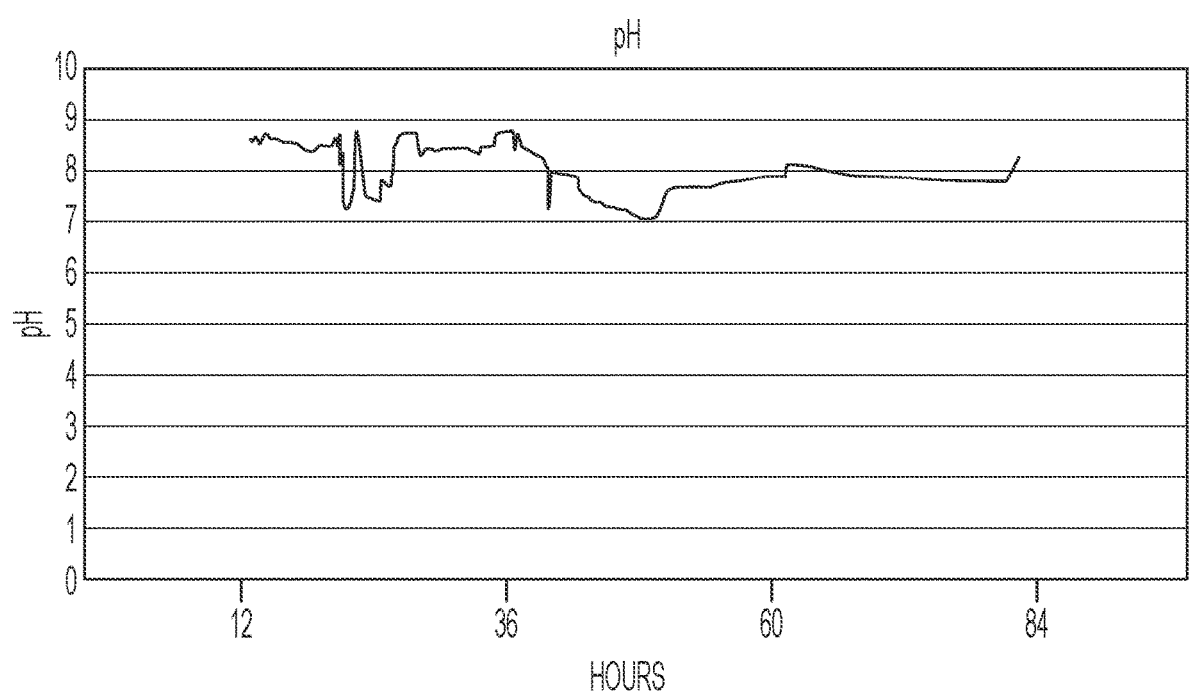
FIG. 8 is a graphical depiction of pH as a function of time obtained from a pH probe in accordance with the present disclosure.

With particular respect to FIG. 6, a graphical depiction of total conductivity as a function of time obtained from the conductivity probe 40 shows that the ion/salt concentration is relatively stable for the measured time period along the flow path of the surface wellbore fluid circulating system 11. With particular respect to FIG. 7, a graphical depiction of total conductivity response of a number of exemplary salts as a function of time (salt curve) obtained from the conductivity probe 40 is shown, indicating that measured conductivity in FIG. 6 represents as fluid density of about 1,228 kg/m3 for a CaCl2 brine. With particular respect to FIG. 8, a graph of pH as a function of time obtained from the pH probe 36 shows that the pH in the system begins higher as lime is added to raise pH, but begins to settle lower as the system buffers.

Example 2

Figure 9:
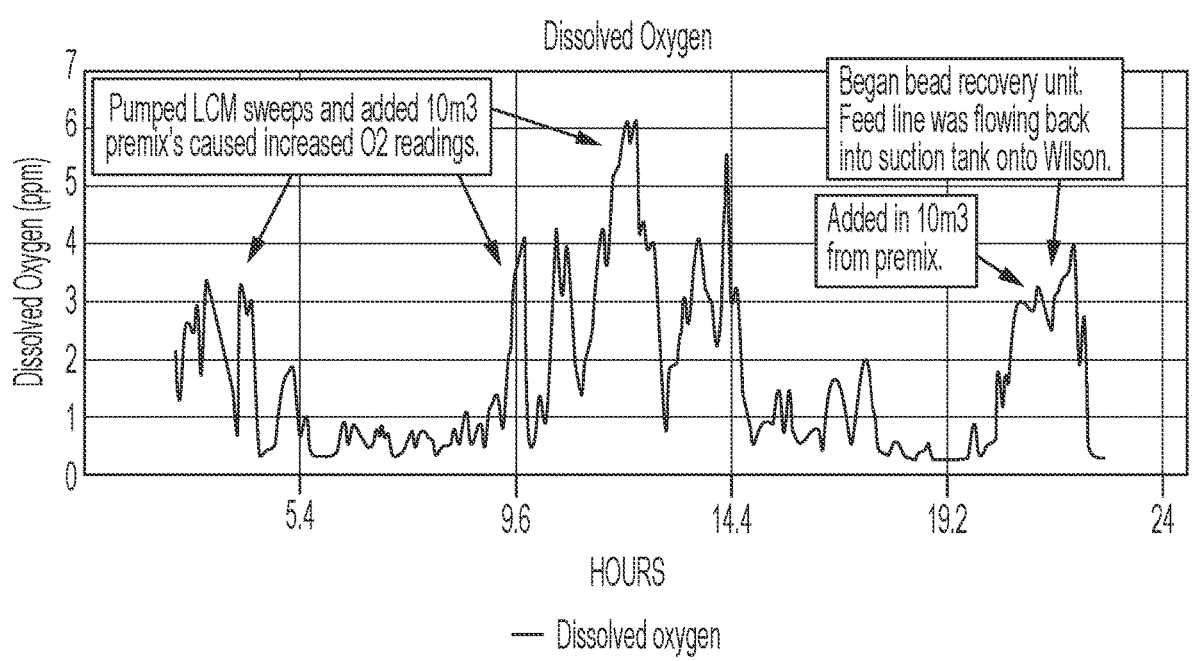
FIG. 9 is a graphical depiction of dissolved oxygen concentration as a function of time obtained from a dissolved oxygen probe in accordance with the present disclosure.
Figure 10:
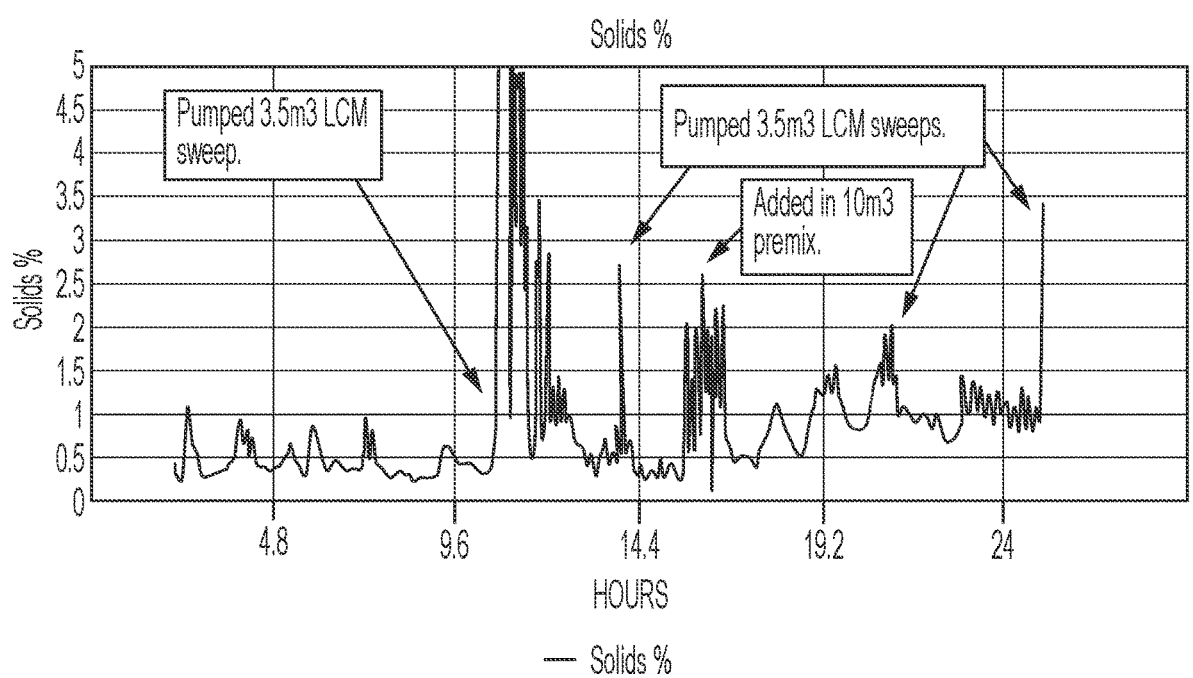
FIG. 10 a graphical depiction of total suspended solids as a function of time obtained from a turbidity probe in accordance with the present disclosure.
Figure 11:
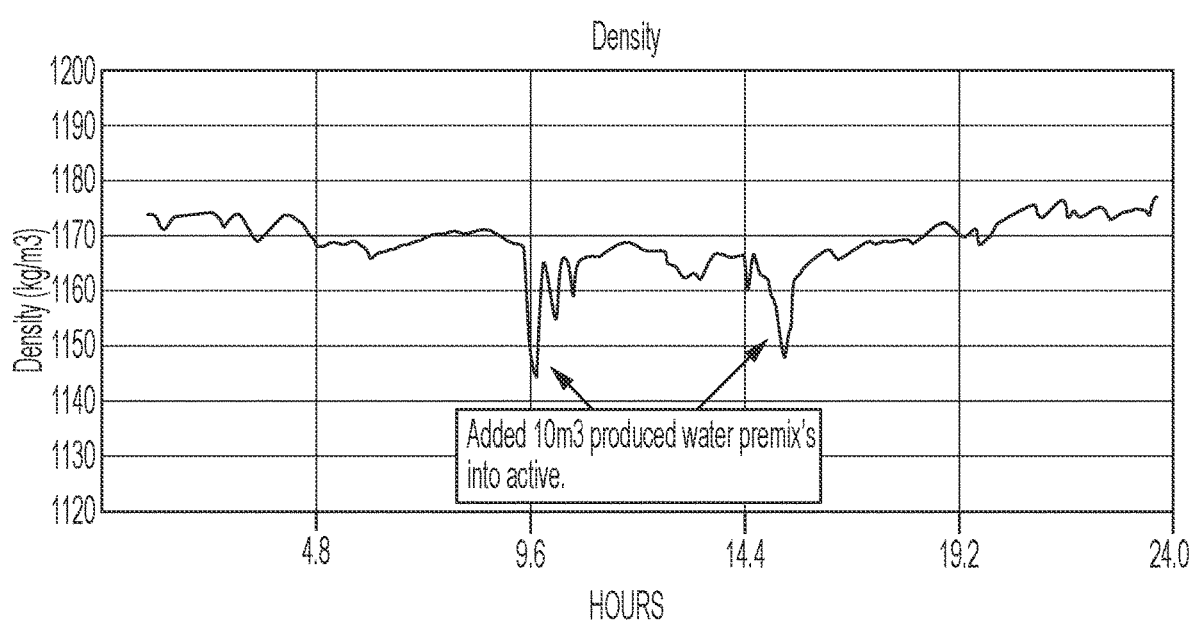
FIG. 11 is a graphical depiction of density as a function of time obtained from the combined output of a conductivity probe and a turbidity probe in accordance with the present disclosure.
Figure 12:
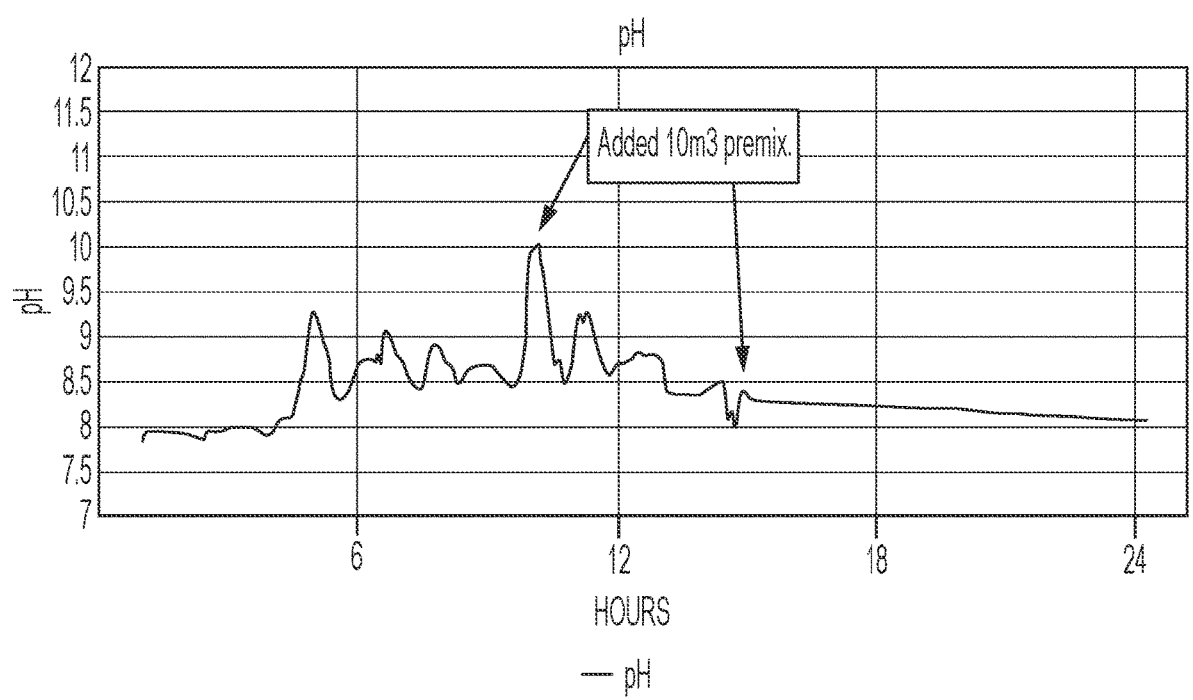
FIG. 12 is a graphical depiction of pH as a function of time obtained from a pH probe in accordance with the present disclosure.

In this example, the probe array 26 was equipped with the dissolved oxygen probe 34, the pH probe 36, the turbidity probe 38, and the conductivity probe 40 was used to monitor wellbore at a drilling site at various locations in the surface wellbore fluid circulating system 11. Measurements were obtained continuously for two days. In contrast to Example 1, the probe array 26 was deployed in the suction tank 20 for all times indicated. With particular respect to FIG. 9, a graphical depiction of dissolved oxygen changes over time is shown. With particular respect to FIG. 10, a graphical depiction of total suspended solids as a function of time obtained from the turbidity probe 38 is shown. With particular respect to FIG. 11, a graphical depiction of total conductivity as a function of time obtained from the conductivity probe 40 is shown. With particular respect to FIG. 12, a graph of pH as a function of time obtained from a pH module shows that the pH in the system begins higher as lime is added to raise pH, but begins to settle lower as the system buffers.

We claim:

1. A probe array system for monitoring one or more fluid properties of a wellbore fluid in a pit or tank comprising:
   a buoyant flotation device configured to maintain the probe array adjacent a surface of the wellbore fluid;
   an acquisition module secured to the bottom of the flotation device such that the acquisition module is positioned below the surface of the wellbore fluid during monitoring of the fluid regardless of changes in fluid level in the pit or tank and wherein the acquisition module comprises one or more of a dissolved oxygen probe, a pH probe, a turbidity probe, or a conductivity probe;
   a transmitter configured to receive data acquired from the acquisition module and transmit the data to a computer system configured to receive the data from the transmitter and configured to perform the steps of:
   processing the data to determine one or more wellbore fluid properties, and
   displaying the one or more wellbore fluid properties.

2. The probe array of claim 1, wherein processing the data to determine one or more fluid properties comprises determining a corrosion rate.

3. The probe array of claim 1, wherein the computer system is further configured to display one or more remedial actions.

4. The probe array of claim 3, wherein the one or more remedial actions comprises raising a fluid level in one or more tanks containing the wellbore fluid to reduce dissolved oxygen.

5. The probe array of claim 3, wherein the one or more remedial actions comprises at least one of the following:
   (a) adding salts to increase conductivity of the wellbore fluid;
   (b) the addition of an oxygen scavenger to reduce dissolved oxygen;
   (c) changing location of the probe array; or
   (d) adding a flocculant to reduce turbidity.

6. The probe array of claim 3, wherein the one or more remedial actions comprises adding a caustic to increase pH.

7. The probe array of claim 3, wherein the one or more remedial actions comprises adding a caustic to reduce turbidity.

8. The method of claim 1, wherein the probe array comprises a flotation device.

9. The method of claim 1, wherein the probe array comprises a protective cage.

10. The method of claim 1, wherein the probe array is coupled to a transmitter.

11. A method comprising:
   (a) measuring one or more fluid properties of a wellbore fluid in a container containing the wellbore fluid using a probe, array comprising a flotation device and an acquisition module positioned below the flotation device wherein the acquisition module remains submerged in the wellbore fluid and includes probes for measuring dissolved oxygen, pH, turbidity, or conductivity;
   (b) maintaining the probe array adjacent to a surface of the wellbore fluid and determining a change in the one or more fluid properties of the wellbore fluid over a time interval from the measured fluid properties; and
   (c) performing a remedial action to change the one or more fluid properties.

12. The method of claim 11, wherein the step of measuring occurs at or adjacent to a location in which the wellbore fluid enters a wellbore.

13. The method of claim 11, wherein the step of measuring comprises measuring the one or more fluid properties in real time.

14. The method of claim 11, wherein the probe array is emplaced within a suction tank.

15. The method of claim 11, wherein the probe array is emplaced within a flocculation tank.

16. The method of claim 11, wherein determining a change in the one or more fluid properties of the wellbore fluid over a time interval comprises determining a corrosion rate.

17. The method of claim 11, wherein the remedial action comprises adjusting one or more of pH, additive concentration, brine concentration, and fluid level within the container.

18. A probe array system for monitoring one or more properties of a wellbore fluid comprising:
- a buoyant flotation device configured to maintain the probe at the surface of the wellbore fluid in a pit or tank being monitored wherein the probe array consists of multiple probes for measuring or monitoring the wellbore fluid;
- an acquisition module secured to the flotation device such that the acquisition module is positioned below the surface of the wellbore fluid and is capable of functioning in the measurement or monitoring of a physical property of the wellbore fluid;
- a protective cage surrounding the flotation device functioning to provide impact protection to the flotation device and acquisition module while allowing wellbore fluid into the flotation device and acquisition module;
- a transmitter configured to receive data acquired from the acquisition module and transmit the data to a computer system configured to receive the data from the transmitter and configured to perform the steps of:
  - processing the data to determine one or more wellbore fluid properties, and
    - displaying the one or more wellbore fluid properties; and
- one or more cables capable of transferring data from the acquisition module to the computer system.

19. The probe array system of claim 18, wherein the acquisition module comprises one or more of the following: a dissolved oxygen probe, pH probe, turbidity probe or conductivity probe.

20. The probe array system of claim 18, wherein the acquisition module comprises one of more of the following; an emulsion strength probe, capacitance probe, dielectric probe, impedance probe, loss tangent probe, reactance phase angle probe, acoustic attenuation probe, acoustic relaxation probe, salinity probe, oil content probe, solids content probe or water content probe.

* * * * *